United States Patent
Deane et al.

(10) Patent No.: US 11,786,328 B2
(45) Date of Patent: Oct. 17, 2023

(54) CONTROLLING A SURGICAL INSTRUMENT

(71) Applicant: CMR SURGICAL LIMITED, Cambridge (GB)

(72) Inventors: Gordon Thomas Deane, Cambridge (GB); Graham John Veitch, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 585 days.

(21) Appl. No.: 17/066,000

(22) Filed: Oct. 8, 2020

(65) Prior Publication Data

US 2021/0106395 A1 Apr. 15, 2021

(30) Foreign Application Priority Data

Oct. 11, 2019 (GB) ...................................... 1914738

(51) Int. Cl.
  *A61B 34/35* (2016.01)
  *A61B 34/37* (2016.01)
  (Continued)

(52) U.S. Cl.
  CPC .............. *A61B 34/35* (2016.02); *A61B 34/37* (2016.02); *A61B 34/71* (2016.02); *A61B 34/74* (2016.02); *B25J 15/0028* (2013.01); *A61B 17/29* (2013.01)

(58) Field of Classification Search
  CPC ......... A61B 34/35; A61B 34/71; A61B 34/74; A61B 17/29; A61B 34/30; A61B 34/77; A61B 34/70; B25J 15/0028
  See application file for complete search history.

(56) References Cited

U.S. PATENT DOCUMENTS 10,166,082 B1 * 1/2019 Hariri ................... A61B 34/71
2013/0103199 A1 4/2013 Kim et al.
(Continued)

FOREIGN PATENT DOCUMENTS

CA  3082493 A1  5/2019
CN  103209657 A  7/2013
(Continued)

OTHER PUBLICATIONS

United Kingdom Search Report from corresponding United Kingdom Application No. GB1914738.8 dated Mar. 11, 2020.
(Continued)

*Primary Examiner* — Julian W Woo
(74) *Attorney, Agent, or Firm* — Lando & Anastasi, LLP (57) ABSTRACT

A control system configured to control manipulation of a surgical instrument in response to manipulation of a remote surgeon input device. The surgical instrument comprises opposable first and second end effector elements connected to a shaft by an articulated coupling. The articulated coupling comprises a first joint driveable by a first pair of driving elements so as to permit the first end effector element to rotate, and a second joint driveable by a second pair of driving elements so as to permit the second end effector element to rotate. The control system: responds to a closing motion of the surgeon input device by commanding maximum forces to be applied to the first and second pairs of driving elements, so as to cause the first and second end effector elements to rotate in opposing rotational directions towards each other with a maximum closing force; and on detecting that the closing motion of the surgeon input device has ceased, commanding a reduction in the force applied to the first and second pairs of driving elements, thereby enabling both the first and second end effector elements to
(Continued)

be rotated in the same rotational direction in response to a yawing motion of the surgeon input device.

27 Claims, 6 Drawing Sheets

(51) Int. Cl.
  *A61B 34/00* (2016.01)
  *B25J 15/00* (2006.01)
  *A61B 17/29* (2006.01)

(56) References Cited

U.S. PATENT DOCUMENTS

| | | |
|---|---|---|
| 2018/0214223 A1 | 8/2018 | Turner |
| 2019/0142531 A1 | 5/2019 | Wentworth et al. |
| 2020/0188045 A1* | 6/2020 | Overmyer .............. A61B 34/76 |
| 2021/0259793 A1* | 8/2021 | Richmond ............. A61B 34/30 |

FOREIGN PATENT DOCUMENTS

| | | |
|---|---|---|
| EP | 2901960 A1 | 8/2015 |
| GB | 2560384 A | 9/2018 |
| WO | 2017098273 A1 | 6/2017 |
| WO | 2018055352 A1 | 3/2018 |
| WO | 2019000090 A1 | 1/2019 |
| WO | 2019130089 A1 | 7/2019 |

OTHER PUBLICATIONS

Japanese Notification of Reasons for Refusal from corresponding Japanese Application No. 2022-521417 dated May 9, 2023.
Notification of Transmittal of the International Search Report and the Written Opinion of the International Searching Authority from corresponding PCT/GB2020/052531 dated Mar. 5, 2021.
Partial International Search Report from corresponding PCT/GB2020/052531 dated Dec. 18, 2020.
Indian Examination Report from corresponding Indian Application No. 202228065735 dated Feb. 7, 2023.

* cited by examiner

CONTROLLING A SURGICAL INSTRUMENT

CROSS-REFERENCE TO RELATED APPLICATION

This application claims the benefit under 35 U.S.C. § 119 of United Kingdom Patent Application No. 1914738.8 filed on Oct. 11, 2019 which is hereby incorporated herein by reference in its entirety for all purposes.

BACKGROUND

Figure 1:
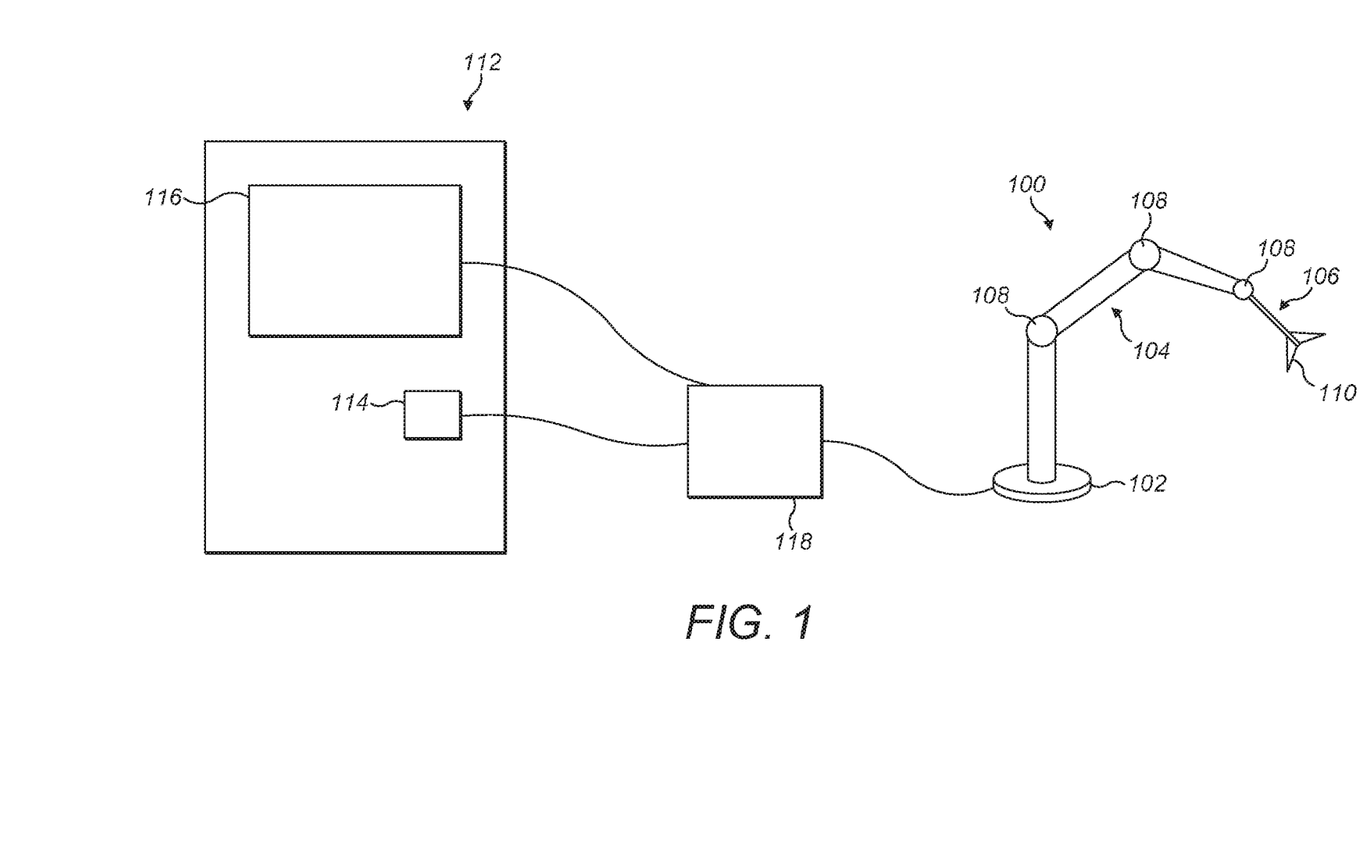
FIG. 1 illustrates a surgical robot system for performing a surgical procedure.

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. At its distal end, the instrument comprises an end effector 110 for engaging in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly.

It is known for the jaws of an end effector to be individually driven by cables. These cables may be utilised to drive opening and closing of the jaws so as to grip and release an object between them. The same cables may also be used to drive a yawing motion of the jaws so as to cause the jaws to rotate in the same direction with the opening angle of the jaws remaining constant. Since the same cables are used to drive both the gripping and yawing motion of the jaws, these operations are not independent. As a result of this, the whole range of gripping motion cannot be accessed over the whole range of yawing motion, and vice versa.

Thus, there is a need for a control system which better mediates the interdependence of the gripping and yawing motion of an end effector.

SUMMARY OF THE INVENTION

According to a first aspect of the invention, there is provided a control system for controlling manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to: respond to a closing motion of the surgeon input device by commanding maximum forces to be applied to the first and second pairs of driving elements, so as to cause the first and second end effector elements to rotate in opposing rotational directions towards each other with a maximum closing force; and on detecting that the closing motion of the surgeon input device has ceased, commanding a reduction in the force applied to the first and second pairs of driving elements, thereby enabling both the first and second end effector elements to be rotated in the same rotational direction in response to a yawing motion of the surgeon input device.

The surgeon input device may comprise a body and a trigger, and the closing motion of the surgeon input device comprise a movement of the trigger relative to the body.

The closing motion of the surgeon input device may comprise a rotation of the trigger towards the body.

The closing motion of the surgeon input device may comprise a linear translation of the trigger relative to the body.

The yawing motion may comprise a rotation of the body of the surgeon input device.

The surgeon input device may comprise a sensor for detecting the position of the trigger relative to the body, wherein the control system detects that the closing motion of the surgeon input device has ceased if the sensed position of the trigger relative to the body is constant.

The control system may comprise a single-pole filter which receives a velocity of the trigger derived from the sensed positions of the trigger relative to the body, and outputs a force reduction factor.

The control system may be configured to command maximum forces to be applied to the first and second pairs of driving elements by: applying a first maximum force to a first driving element of the first pair of driving elements, and applying a second maximum force to a second driving element of the second pair of driving elements, wherein the magnitudes of the first and second maximum forces are the same.

The control system may be configured to command maximum forces to be applied to the first and second pairs of driving elements by: applying a first maximum force to a first driving element of the first pair of driving elements, and applying a second maximum force to a second driving element of the second pair of driving elements, wherein the magnitudes of the first and second maximum forces are different.

The first and second maximum forces may be tension forces.

Each of the first and second pairs of driving elements may comprise cables.

The control system may be configured to command a reduction in the force applied to the first and second pairs of driving elements by a function dependent on instrument type and/or trigger motion.

The maximum closing force may enable cutting of an object between the first and second end effector elements.

Upon the control system detecting that the closing motion of the surgeon input device has ceased, the first and second end effector elements may abut each other in a closed configuration.

The control system may be configured to respond to a yawing motion of the surgeon input device by commanding: a first force to be applied to the first driving element of the first pair of driving elements, and a second force to be applied to the first driving element of the second pair of driving elements, wherein the magnitudes of the first and second forces are the same.

The opposable first and second end effector elements may be a pair of scissors. The pair of scissors may be a pair of curved scissors. The pair of scissors may be a pair of monopolar scissors.

According to a second aspect of the invention, there is provided a control system for controlling manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to: respond to a gripping configuration of the surgeon input device by commanding maximum forces to be applied to the first and second pairs of driving elements, so as to cause the first and second end effector elements to rotate in opposing rotational directions towards each other with a maximum closing force; and on detecting a yawing motion of the surgeon input device, commanding a reduction in the force applied to a first driving element of the first pair of driving elements, thereby enabling both the first and second end effector elements to be rotated in the same rotational direction.

On detecting the yawing motion of the surgeon input device, the control system may be configured to continue commanding the maximum force to be applied to a second driving element of the second pair of driving elements.

The surgeon input device may comprise a body and a trigger, and the surgeon input device may be in a gripping configuration when the trigger has a position relative to the body that is within a specified range.

The gripping configuration of the surgeon input device may comprise a rotational position of the trigger relative to the body that is within a specified range of rotational positions.

The gripping configuration of the surgeon input device may comprise a linear position of the trigger relative to the body that is within a specified range of linear positions.

The yawing motion may comprise a rotation of the body of the surgeon input device.

The surgeon input device may comprise a sensor for detecting the position of the trigger relative to the body.

The control system may comprise a single-pole filter which receives a velocity of the trigger derived from the sensed positions of the trigger relative to the body, and outputs a force reduction factor.

The control system may command maximum forces to be applied to the first and second pairs of driving elements by: applying a first maximum force to a first driving element of the first pair of driving elements, and applying a second maximum force to a second driving element of the second pair of driving elements, wherein the magnitudes of the first and second maximum forces are the same.

The control system may command maximum forces to be applied to the first and second pairs of driving elements by: applying a first maximum force to a first driving element of the first pair of driving elements, and applying a second maximum force to a second driving element of the second pair of driving elements, wherein the magnitudes of the first and second maximum forces are different.

The first and second maximum forces may be tension forces.

Each of the first and second pairs of driving elements may comprise cables.

The control system may be configured to command a reduction in the force applied to the first and second pairs of driving elements by a function dependent on instrument type and/or trigger motion.

The maximum closing force may enable gripping of an object between the first and second end effector elements.

The opposable first and second end effector elements may be a needle holder. The opposable first and second end effector elements may be a pair of jaws.

According to a third aspect of the invention, there is provided a control system for controlling manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to: respond to a closing motion of the surgeon input device by: comparing a demanded first yaw torque for the first end effector element to a first maximum yaw torque, and comparing a demanded second yaw torque for the second end effector element to a second maximum yaw torque, and only if the demanded first yaw torque is less than the first maximum yaw torque, and the demanded second yaw torque is less than the second maximum yaw torque, commanding the demanded first yaw torque to be applied to the first end effector element and the demanded second yaw torque to be applied to the second end effector element, so as to cause the first and second end effector elements to rotate in opposing rotational directions towards each other with a closing force; and on detecting a yawing motion of the surgeon input device, command co-directional forces to be applied to the first and second pairs of driving elements, thereby causing both the first and second end effector elements to be rotated in the same rotational direction.

The control system may, if the demanded first yaw torque is greater than the first maximum yaw torque, and the demanded second yaw torque is greater than the second maximum yaw torque, command the first maximum yaw torque to be applied to the first end effector element and the second maximum yaw torque to be applied to the second end effector element, so as to cause the first and second end effector elements to rotate in opposing rotational directions towards each other with a closing force.

The control system may further respond to a closing motion of the surgeon input device by: comparing the demanded first yaw torque for the first end effector element to a first minimum yaw torque, and comparing a demanded second yaw torque for the second end effector element to a second minimum yaw torque, and only if the demanded first yaw torque is greater than the first minimum yaw torque, and the demanded second yaw torque is greater than the second minimum yaw torque, commanding the demanded first yaw torque to be applied to the first end effector element and the demanded second yaw torque to be applied to the second end effector element, so as to cause the first and second end effector elements to rotate in opposing rotational directions towards each other with a closing force.

The control system may, if the demanded first yaw torque is less than the first minimum yaw torque, and the demanded second yaw torque is less than the second minimum yaw torque, command the first minimum yaw torque to be applied to the first end effector element and the second minimum yaw torque to be applied to the second end effector element, so as to cause the first and second end effector elements to rotate in opposing rotational directions towards each other with a closing force.

BRIEF DESCRIPTION OF THE FIGURES

The present invention will now be described by way of example with reference to the accompanying drawings. In the drawings.

DETAILED DESCRIPTION

The following describes controlling a surgical robotic instrument from a remote surgeon console. The instrument and console form part of a surgical robotic system of the type illustrated in FIG. 1.

The surgical instrument is supported by a robot arm. The robot arm is itself supported by a base. During surgery, the base is secured to part of the operating theatre, for example the floor, ceiling, cart or patient bed. The robot arm remains at all times external to the patient. The robot arm comprises a series of arm links interspersed with joints. These joints may be revolute joints. The end of the robot arm distal to the base can be articulated relative to the base by movement of one or more of the joints. The surgical instrument attaches to a drive assembly at the distal end of the robot arm. This attachment point is external to the patient.

The surgical instrument has an elongate profile, with a shaft spanning between its proximal end which attaches to the robot arm and its distal end which accesses the surgical site within the patient body. The proximal end of the surgical instrument and the instrument shaft may be rigid with respect to each other and rigid with respect to the distal end of the robot arm when attached to it. An incision is made into the patient body, through which a port is inserted. The surgical instrument may penetrate the patient body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface engage individual drive assembly interface elements of the drive assembly. The instrument interface is releasably engageable with the drive assembly. The instrument can be detached from the robot arm manually without requiring any tools. This enables the instrument to be detached from the drive assembly quickly and another instrument attached during an operation.

Figure 2:
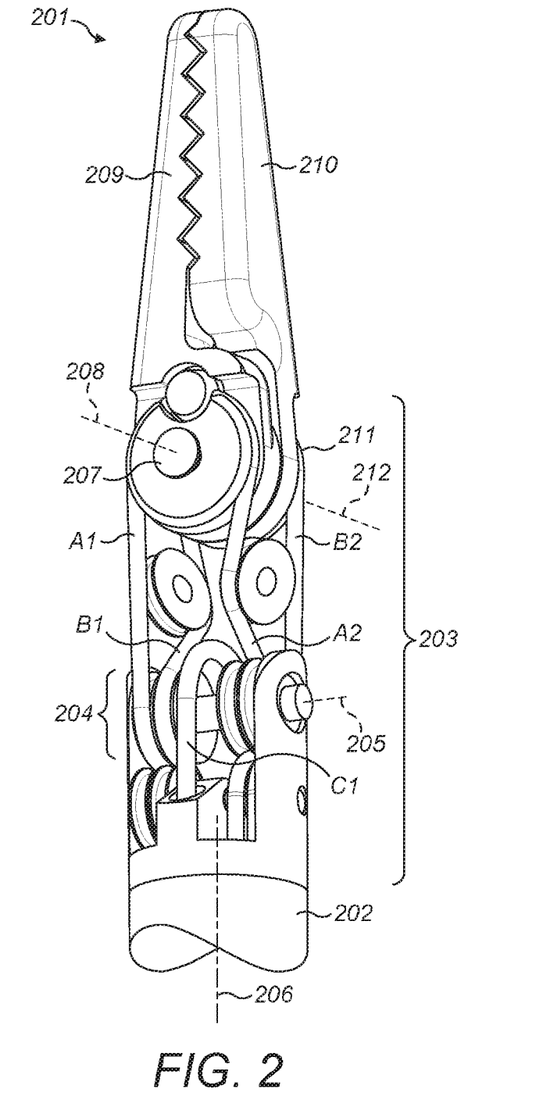
FIG. 2 illustrates the distal end of an exemplary surgical instrument.

At the distal end of the surgical instrument, the shaft is connected to an end effector by an articulated coupling. The end effector engages in a surgical procedure at the surgical site. FIG. 2 illustrates the distal end of an exemplary instrument which has a pair of jaws as the end effector 201. The shaft 202 is connected to the end effector 201 by articulated coupling 203. The articulated coupling 203 comprises several joints. These joints enable the pose of the end effector to be altered relative to the direction of the instrument shaft. The end effector may also comprise joint(s). In the example of FIG. 2, the articulated coupling 203 comprises a pitch joint 204. The pitch joint 204 rotates about pitch axis 205, which is perpendicular to the longitudinal axis 206 of the shaft 202. The pitch joint 204 permits a supporting body (described below) and hence the end effector to rotate about the pitch axis 205 relative to the shaft. In the example of FIG. 2, the end effector comprises a first yaw joint 207 and a second yaw joint 211. First yaw joint 207 rotates about first yaw axis 208. Second yaw joint 211 rotates about second yaw axis 212. Both yaw axes 208 and 212 are perpendicular to pitch axis 205. Yaw axes 208 and 212 may be parallel. Yaw axes 208 and 212 may be collinear. The articulated coupling 203 comprises a supporting body. At one end, the supporting body is connected to the shaft 202 by pitch joint 204. At its other end, the supporting body is connected to the end effector 201 by the yaw joints 207 and 211. This supporting body is omitted from FIG. 2 for ease of illustration so as to enable the other structure of the articulated coupling to be more easily seen. The end effector comprises two end effector elements 209, 210. The end effector elements shown are opposing jaws. However, the end effector elements may be any type of opposing end effector elements, further examples of which are discussed later. The first yaw joint 207 is fast with the first end effector element 209 and permits the first end effector element 209 to rotate about the first yaw axis 208 relative to the supporting body and the pitch joint 204. The second yaw joint 211 is fast with the second end effector element 210 and permits the second end effector element 210 to rotate about the second yaw axis 212 relative to the supporting body and the pitch joint 204.

The joints illustrated in FIG. 2 are driven by pairs of driving elements. The driving elements are elongate. They are flexible transverse to their longitudinal extent. They resist compression and tension forces along their longitudinal extent. Each pair of driving elements is secured at the other end of the instrument shaft to a respective instrument interface element of the instrument interface. Thus, the robot arm transfers drive to the end effector as follows: movement of a drive assembly interface element moves an instrument interface element which moves a driving element which moves one or more joint of the articulation and/or end effector which moves the end effector. The driving elements may be cables. The driving elements may comprise flexible portions and a rigid portion. Flexible portions engage the components of the instrument interface and the articulated coupling, and the rigid portion extends through all or part of the instrument shaft. For example, the flexible portion may be a cable, and the rigid portion may be a spoke.

FIG. 2 illustrates a first pair of driving elements A1, A2 which are constrained to move around the first yaw joint 207. Driving elements A1, A2 drive rotation of the first end effector element 209 about the first yaw axis 208. FIG. 2 illustrates a second pair of driving elements B1, B2 which are constrained to move around the second yaw joint 211. Driving elements B1, B2 drive rotation of the second end effector element 210 about the second yaw axis 212. FIG. 2 also illustrates a third pair of driving elements C1, C2 which are constrained to move around pitch joint 204. Driving elements C1, C2 drive rotation of the end effector 201 about the pitch axis 205. The pitch joint 204 and yaw joints 207, 211 are independently driven by their respective driving elements.

The end effector elements 209 and 210 are independently rotatable. The end effector elements can be rotated in opposing rotational directions. For example, the end effector elements can be rotated in opposing rotational directions towards each other by applying tension to driving elements A2 and B1. This closes the end effector elements together, which is useful for (i) gripping an object between the end effector elements, such as tissue or a needle or thread, and/or (ii) cutting an object between the end effector elements, such as tissue or thread. The end effector elements can be rotated in opposing rotational directions away from each other by applying tension to driving elements A1 and B2. This opens the end effector elements, which is useful for (i) releasing an object which has been grasped between the end effector elements, and/or (ii) reopening a pair of scissor end effector elements ready for another cutting action. Both end effector elements can be rotated in the same rotational direction, by applying tension to driving elements A1 and B1 or alternatively A2 and B2. This causes the end effector elements to yaw about the pivot axes 208 and 212. This is useful for enabling the end effector to access a different part of the surgical site. Alternatively, one end effector element can be rotated (in either rotational direction) whilst the other end effector element is maintained in position, by applying tension to only one of driving elements A1, A2, B1, B2. Thus, both a gripping motion and a yawing motion of the end effector is enabled by manipulating the same pairs of driving elements: A1, A2 for the first end effector element 209, and B1, B2 for the second end effector element 210.

There are at least two types of instruments having opposable end effectors which are relevant to the following description. The first type is cutting instruments, for which the end effector elements engage so as to cut tissue or another object between the end effector elements. The second type is gripping instruments, for which the end effector elements engage so as to grasp tissue or another object between the end effector elements.

The surgeon console comprises one or more surgeon input devices. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

Figure 3:
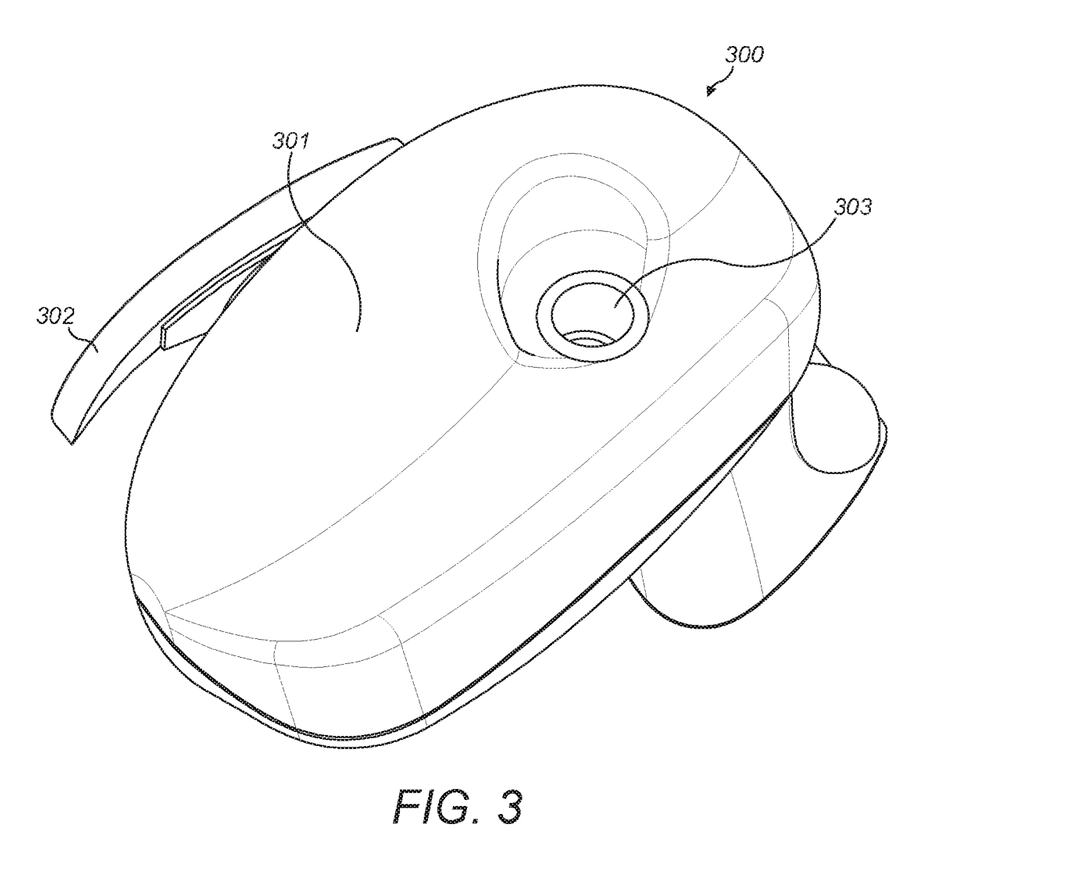
FIG. 3 illustrates an exemplary surgeon input device.

FIG. 3 illustrates an exemplary hand controller 300. The hand controller is connected to the surgeon console, for example by a gimbal arrangement (not shown). This enables the hand controller to be moved with three degrees of translational freedom with respect to the surgeon console. The hand controller shown is intended to be held by a right hand. A mirror image hand controller could be held by a left hand. The hand controller comprises a body 301 suitable for being gripped by a hand. The hand controller may comprise additional inputs, for example buttons, switches, levers, slide inputs or track pads 303. The hand controller of FIG. 3 comprises a trigger 302. The trigger 302 is movable relative to the body 301. In the hand controller shown, the trigger 302 is rotatable relative to the body 301. Alternatively, or in addition, the trigger could translate linearly relative to the body 301.

The surgeon may rotate the trigger 302 relative to the body 301 of the hand controller in order to command the end effector elements 209, 210 of the instrument to close in a gripping/closing motion or to open in a releasing/opening motion. For example, the surgeon may rotate the trigger 302 towards the body 301 of the hand controller to command a gripping motion. The surgeon may rotate the trigger 302 away from the body 301 of the hand controller to command a releasing motion. The surgeon may rotate the body of the hand controller in the hand controller workspace to command a change in orientation of the end effector elements.

A control system connects the surgeon console to the surgical robot. The control system comprises a processor and a memory. The memory stores, in a non-transient way, software code that can be executed by the processor to cause the processor to control the surgeon console and robot arm and instrument in the manner described herein. The control system receives the inputs from the surgeon input device(s) and converts these to control signals to move the joints of the robot arm and/or the joint(s) of the articulated coupling and/or the joint(s) of the end effector. The control system sends these control signals to the robot arm, where the corresponding joints are driven accordingly. Manipulation of the surgical instrument is thereby controlled by the control system in response to manipulation of the surgeon input device.

When the control system is controlling a cutting instrument, on detecting a closing motion of the hand controller, the control system responds by commanding a force to be applied to the driving elements of the end effector elements to cause the end effector elements to rotate in opposing rotational directions towards each other. Referring to FIG. 2, the control system responds to detecting the closing motion by commanding a force to be applied to A2 and B1, thereby causing the end effector elements to close together.

When the control system is controlling a gripping instrument, on detecting that the hand controller is in a gripping configuration, the control system responds by commanding a force to be applied to the driving elements of the end effector elements to cause the end effector elements to rotate in opposing rotational directions towards each other. Referring to FIG. 2, the control system responds to detecting the gripping configuration by commanding a force to be applied to A2 and B1, thereby causing the end effector elements to close together. The gripping configuration of the hand controller is one in which the rotational position of the trigger relative to the body is within a specified range. The specified range may be predetermined. The specified range may be dependent on the instrument type. For the case that the trigger translates linearly relative to the body, the gripping configuration of the hand controller is one in which the linear position of the trigger relative to the body is within a specified range. The specified range may be dependent on the instrument type. The specified range may be predetermined.

For a gripping action, a high gripping force of the end effector elements may be desirable. For example, if the end effector is a needle driver, then a high gripping force is desirable to enable holding a needle firmly whilst driving into tissue. As another example, if the end effector is a pair of scissors, then a high closing force is desirable to enable successful cutting of tissue. Thus, the control system responds to detecting a gripping configuration of the hand controller (for a gripping instrument) or a closing motion of the hand controller (for a cutting instrument) by commanding a maximum force to be applied to the driving elements so as to cause a maximum closing force of the end effector elements. Referring to FIG. 2, the control system responds by commanding a maximum force to be applied to A2 and a maximum force to be applied to B1. This results in the end effector elements 209 and 210 rotating towards each other with a maximum closing force, and thereby enabling the end effector to grip/cut with maximum force.

If the driving elements are driven in tension, as in the example of FIG. 2, then the maximum forces applied to the driving elements are tension forces. Each maximum force is the maximum tension force that can be applied to that driving element without it failing, for example by stretching or snapping. If the driving elements are driven in compression, then the maximum force applied to the driving elements are compression forces. Each maximum force is the maximum compression force that can be applied to that driving element without it failing, for example by compressing or fracturing. If the driving elements are driven in both tension and compression, for example if they are push rods, then a maximum tension force and a maximum compression force are defined. The maximum tension force is the maximum force that can be applied to the driving element in tension without it failing. The maximum compression force is the maximum force that can be applied to the driving element in compression without it failing. If the driving elements are driven in torsion, for example if they are lead screws, then the maximum force applied to the driving elements are torsional forces. Each maximum force is the maximum torsional force that can be applied to that driving element without it failing.

The control system commands a first maximum force to be applied to the driving element driving rotation of the first end effector element towards the second end effector element. In the example of FIG. 2, the control system commands a first maximum force to be applied to A2 to drive end effector element 209 to rotate towards end effector element 210. The control system commands a second maximum force to be applied to the driving element driving rotation of the second end effector element towards the first end effector element. In the example of FIG. 2, the control system commands a second maximum force to be applied to B1 to drive end effector element 210 to rotate towards end effector element 209.

The value of the first maximum force and the value of the second maximum force may be dependent on the instrument type. The first maximum force and the second maximum force may be the same. For example, if the end effector elements match and the driving elements which drive each of those end effector elements match, as in the example of FIG. 2, then the control system may command the same maximum force to be applied to both the first driving element A2 and the second driving element B1. Alternatively, the first maximum force and the second maximum force may be different. For example, if the end effector elements are different, then the first maximum driving force applied to the first end effector element may be different to the second maximum driving force applied to the second end effector element in order to achieve the desired maximum closing force of the end effector elements. An example of this would be an asymmetric instrument such as a stapler.

For gripping instruments, the maximum closing force is sufficient to enable gripping of an object between the first and second end effector elements. This gripping may be under resistive force, for example a needle driver gripping a needle whilst driving the needle firmly into tissue. For example, the maximum closing force may be in the range 10-15N. For cutting instruments, the maximum closing force is sufficient to enable cutting of an object (typically tissue) between the first and second end effector elements. For example, the maximum closing force may be in the range 5-10N.

On detecting a rotation of the body of the hand controller in the hand controller workspace, the control system responds by commanding articulation of any one or combination of: (i) the joints of the surgical robot arm, (ii) the joints of the articulated coupling 203 of the surgical instrument, and (iii) the joints of the end effector. This commanded articulation causes the pose of the end effector to change as directed by the surgeon's rotation of the hand controller.

Thus, the control system may respond to detection of the rotation of the body of the hand controller by, at least in part, commanding a force to be applied to the driving elements of the end effector elements to cause the end effector elements to rotate. For example, referring to FIG. 2, the control system may command a force to be applied to A2 and B2 to cause the end effector elements 209 and 210 to yaw in a clockwise direction. The control system may command a force to be applied to A1 and B1 to cause the end effector elements 209 and 210 to yaw in an anti-clockwise direction. The control system may command the same force to be applied to both A1 and B1 (or A2 and B2). If the end effector elements match, and the driving elements for those end effector elements match, then applying the same force to both A1 and B1 (or A2 and B2) causes both end effectors elements to yaw in unison. The control system may also respond to detection of the rotation of the body of the hand controller by commanding forces to be applied to one of C1 and C2 to cause a rotation of the pitch joint 204. The control system may also respond to detection of the rotation of the body of the hand controller by commanding torques to be applied about one or more of the joints of the robot arm.

The same driving elements A1, A2 and B1, B2 are utilised to drive rotation of the end effector elements for both gripping/cutting an object and yawing the end effector. Thus, the gripping/cutting and yawing operations are not independently driven. As a result of this, when a maximum force is being applied to the driving elements A2 and B1 in a gripping/cutting operation, the end effector elements cannot also be yawed. Considering the example of FIG. 2, when maximum tension is applied to A2 and B1 to cause a gripping/cutting action, it is not also possible to apply tension to A2 and B2 to cause a yawing motion of the end effector elements.

Figure 4:
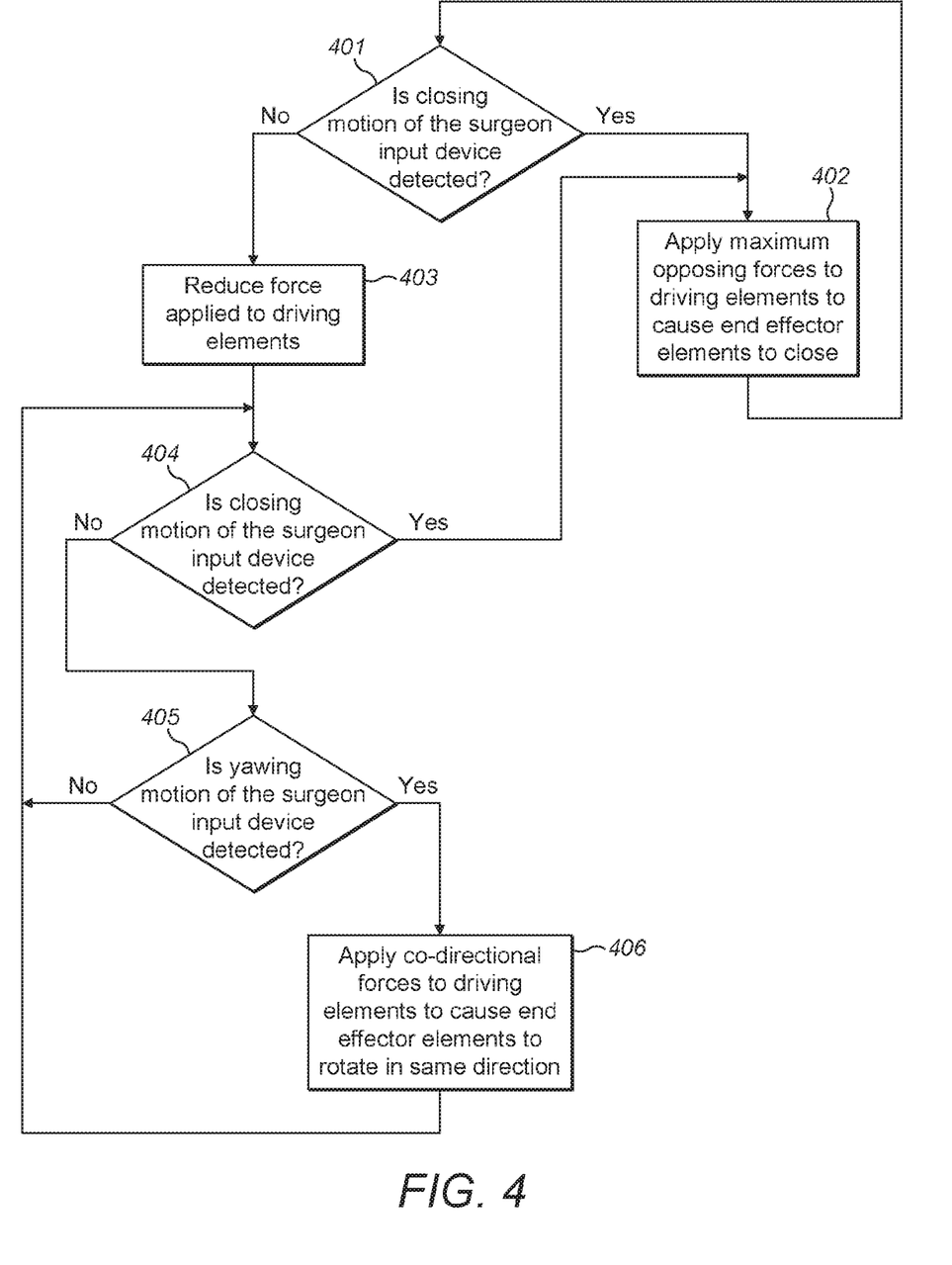
FIG. 4 is a flowchart of a method of controlling manipulation of a surgical instrument.

FIG. 4 illustrates a method implemented by the control system to mediate the interdependence of the cutting and yawing motion of an end effector of a cutting instrument.

At step 401, the control system detects whether there is a closing motion of the surgeon's input device. For the example of the surgeon input device of FIG. 3, the control system detects a closing motion if the trigger 302 is being rotated relative to the body 301 of the hand controller. If the trigger 302 is stationary (anywhere in its rotational range) relative to the body of the hand controller, then the control system determines that there is no closing motion. However, if the trigger 302 is rotating relative to the body 301 of the hand controller, then the control system determines that there is a closing motion.

The hand controller 300 may include a position sensor which senses the rotational position of the trigger 302 relative to the body 301 of the hand controller. The position sensor may sense the rotational position at intervals, for example regular intervals. For example, the sensor may sense the rotational position at a frequency of m kHz. m may be between 10 kHz and 50 kHz. m may be between 25 kHz and 35 kHz. The control system receives the sensed rotational position of the trigger from the position sensor. The sensor may send the sensed position to the control system at intervals, for example regular intervals. For example, the sensor may send the sensed rotational position of the trigger to the control system at a frequency of n kHz. n may be between 1 and 10 kHz. n may be between 3.5 and 6.5 kHz. n may be 5 kHz. The control system determines the velocity of the trigger from the sensed series of rotational positions of the trigger. The control system determines that the closing motion of the hand controller is ongoing if the velocity of the trigger towards the body is greater than 0. The control system determines that the closing motion of the hand controller has ceased if the velocity of the trigger is 0. In other words, the control system determines that the closing motion of the hand controller has ceased if the sensed rotational position of the trigger is constant. The closing motion may have been ceased by the surgeon because the trigger was at the end of its range of motion. This happens when the first and second end effector elements are abutting in a closed configuration. For example, the blades of a pair of scissors have met at the end of a cutting action. Alternatively, the closing motion may have ceased whilst the end effector elements were still in an open configuration. In that open configuration, a further rotation of the end effector elements towards each other and hence towards a closed configuration is possible, but the surgeon stopped the cutting action before the closed configuration was reached.

If at step 401, the control system detects closing motion of the surgeon input device, then it moves to step 402. At step 402, the control system commands maximum opposing forces to be applied to the driving elements of the end effector elements, so as to cause the end effectors to close with a maximum driving force. In the example of FIG. 2, this would be applying maximum driving forces to A2 and B1. Following this, the control loop returns to step 401, where a further assessment is made as to whether the closing motion is detected.

If at step 401, the control system does not detect closing motion of the surgeon input device, then it moves to step 403. At step 403, the control system commands a reduced force to be applied to the driving elements which are causing the end effector elements to close. In the example of FIG. 2, this would be reducing the driving forces applied to A2 and B1.

The factor by which the force is reduced to the driving elements may be dependent on the instrument type. The force reduction value may be solely dependent on instrument type. The force reduction value for each instrument type may be empirically determined. Examples of instrument types for which the force reduction value may be solely dependent on instrument type are jaws and fenestrated graspers. Alternatively, or additionally to instrument type, the factor by which the force is reduced may be dependent on the profile of the trigger motion. Examples of instrument types for which the force reduction value may additionally be dependent on the profile of the trigger motion are needle holders, and scissors such as curved scissors and monopolar scissors.

The control system may comprise a single-pole filter which receives the velocity of the trigger as an input. The single-pole filter utilises the trigger velocity to determine a force reduction value. The parameters of the filter may be instrument type specific. The filter may be linear.

For example, the filter may be a first derivative low pass filter having a weighting value given by:

$$cutWeight[n] = A*cutWeight[n-1] + tposition[n] - tposition[n-1] \quad \text{(equation 1)}$$

where cutWeight[n] is the weighting value for the nth sensed position of the trigger, A is a constant, cutWeight[n−1] is the weighting value for the n−1th sensed position of the trigger, tposition[n] is the nth sensed position of the trigger, and tposition[n−1] is the n−1th sensed position of the trigger. This weighting value provides a threshold which may be used for assessing whether closing motion of the surgeon input device is detected.

If cutWeight[n] is less than a threshold $Y_{CUT}$, then a force reduction value of WEIGHTCUT is applied. If cutWeight[n] is greater than a threshold $Y_{YAW}$, then a force reduction value of WEIGHTYAW is applied. If cutWeight[n] is between $Y_{CUT}$ and $Y_{YAW}$, then a force reduction value of:

$$FRV[n] = WEIGHTYAW - \frac{(WEIGHTYAW - WEIGHTCUT)(Y_{YAW} - cutWeight[n])}{(Y_{YAW} - Y_{CUT})} \quad \text{(equation 2)}$$

where FRV[n] is the force reduction value for the nth sensed position of the trigger.

WEIGHTCUT, WEIGHTYAW, $Y_{CUT}$, $Y_{YAW}$ and A are all constants. For example, WEIGHTCUT may be 0. WEIGHTYAW may be 0.8.

The reduced force applied to the driving elements at step 403 may be given by:

$$\text{Reduced Force}[n] = (1 - FRV[n]) * \text{Maximum Force} \quad \text{(equation 3)}$$

where Reduced Force[n] is the reduced force for the nth sensed position of the trigger, and Maximum Force is the maximum force applied in step 402 following detection of a closing motion of the surgeon's input device.

Thus, in the example that WEIGHTCUT is 0, when cutWeight[n]≤$Y_{CUT}$, no reduction in force is applied to the driving elements, i.e. Reduced Force=Maximum Force. In the example that WEIGHTYAW is 0.8, when cutWeight[n]≥$Y_{YAW}$, an 80% reduction in force is applied to the driving elements, i.e. Reduced Force=0.2*Maximum Force.

When cutWEIGHT is 0, no force reduction is applied to the driving elements. Thus, maximum force can be applied to the closing motion of the end effector elements. When cutWEIGHT is 1, maximum force can be applied to provide yawing motion of the end effector elements.

By reducing the force applied to the driving elements, those driving elements are able to yaw the end effector elements. In the example of FIG. 2, both A1 and B1 (or A2 and B2) can be driven to cause the end effector as a whole to yaw in a clockwise (or anticlockwise) direction. The greater the reduction in the closing force applied to the end effector elements, the greater the speed at which the end effector elements can be yawed. Thus, whilst the control method of FIG. 4 prioritises a closing motion of the end effector, it trades this off against the ability to yaw the end effector elements when the end effector elements are not actively moving towards each other. Maintaining a maximum closing force for a sustained period of time contributes little towards a cutting action, even if the end effector elements have not closed. Thus, once the closing motion has ceased, prioritising the ability of the end effector to yaw has little detrimental effect on a simultaneous cutting action.

Returning to FIG. 4, following the force reduction at step 403, the method moves to step 404. At step 404, the control system determines if a closing motion of the surgeon input device is detected. This step is implemented using the methods described with reference to step 401. If a closing motion is detected, then the control loop moves to step 402, where the control system commands maximum opposing forces to be applied to the driving elements so as to cause the end effector elements to close with a maximum closing force.

However, if at step 404, closing motion is not detected, then the control system moves on to step 405. At step 405, the control system determines if a yawing motion of the surgeon input device is detected. Sensors on the surgeon input device and/or sensors on the linkages connecting the surgeon input device to the console are used to detect a yawing motion of the surgeon input device in the surgeon input device workspace.

If no yawing motion of the surgeon input device is detected, then the method returns to step 404, where the control system determines if a closing motion of the surgeon input device is detected. However, if a yawing motion of the surgeon input device is detected at step 405, then the control loop moves to step 406. At step 406, the control system commands co-directional forces to be applied to the driving elements of the end effector elements so as to cause the end effector elements to rotate in the same direction in accordance with the yawing motion of the surgeon input device. In the example of FIG. 2, this would be applying force to A2 and B2 to cause a clockwise yawing of the end effector elements, and applying force to A1 and B1 to cause an anticlockwise yawing of the end effector elements. In order to carry out the yawing motion commanded by the surgeon input device, the control system may, in addition to commanding the yawing motion of the end effector elements, command articulation of the pitch joint of the articulated coupling 203 and/or articulation of one or more joints of the robot arm.

Whilst the forces are being applied in step 406, the control loop moves to step 404 to determine whether closing motion of the surgeon input device is detected. Acting on a closing motion is a higher priority than acting on a yawing motion. Thus, if a closing motion is detected at step 404 whilst yawing forces are being applied to the driving elements according to step 406, the control system moves to step 402 and overrides the command to yaw the end effector elements with a command to apply maximum forces to the driving elements so as to cause the end effector elements to close together in a closing action with a maximum closing force.

Thus, the control loop of FIG. 4 may be utilised to better mediate the interdependence of the cutting and yawing motion of an end effector. Cutting is prioritised, but yawing is enabled when the surgeon is not actively manipulating the surgeon input device in a closing motion.

Figure 5:
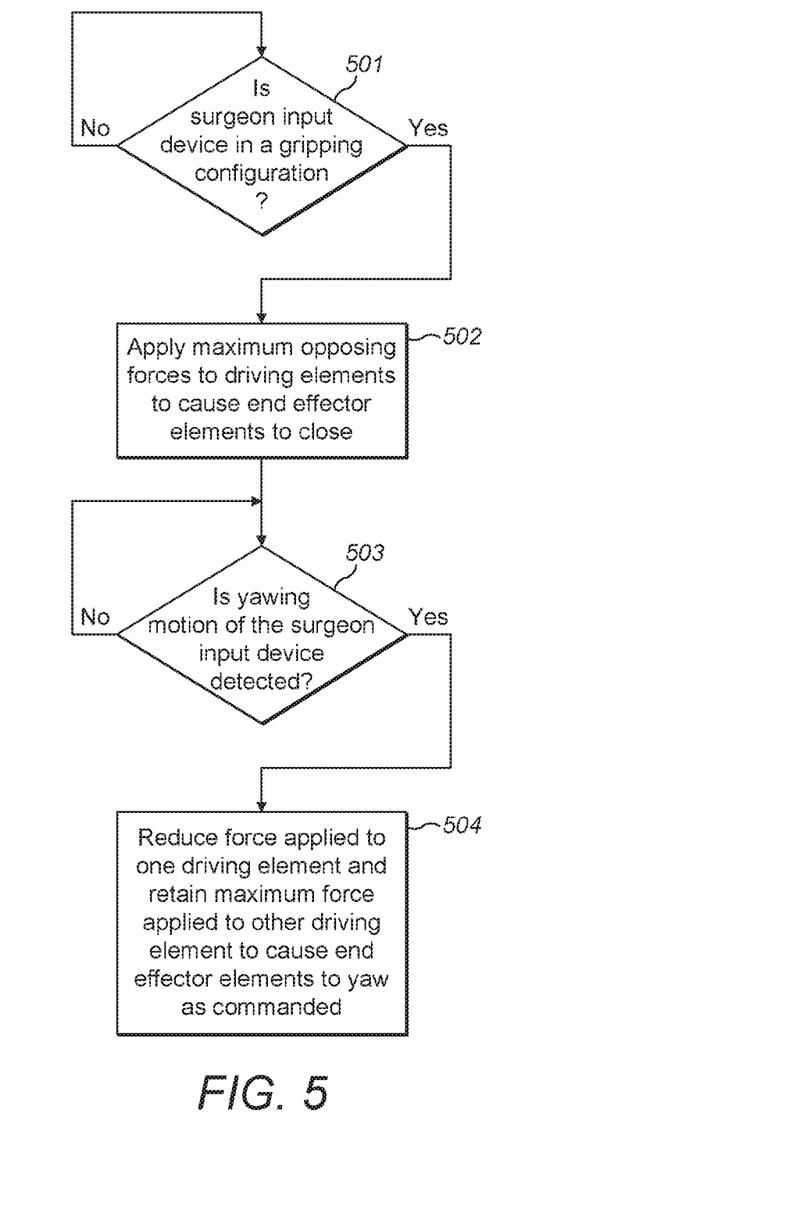
FIG. 5 is a flowchart of a method of controlling manipulation of a further surgical instrument.

FIG. 5 illustrates a method implemented by the control system to mediate interdependence of the gripping and yawing motion of an end effector of a gripping instrument.

At step 501, the control system detects whether the surgeon's input device is in a gripping configuration. For the example of the surgeon input device of FIG. 3, the control system detects a gripping configuration if the rotational position of the trigger 302 relative to the body 301 is within a specified range, as described above. The control system does not detect a gripping configuration if the rotational position of the trigger 302 relative to the body 301 is outside of the specified range.

The control system may periodically receive the sensed rotational position of the trigger from a position sensor on the hand controller as described above with respect to FIG. 4. If the sensed rotational position is within the specified range, then the control system determines that the surgeon input device is in the gripping configuration. If the sensed rotational position is not within the specified range, then the control system determines that the surgeon input device is not in the gripping configuration.

If at step 501, the control system detects that the surgeon input device is not in a gripping configuration, then the control system returns to step 501. The control system may wait for a time interval T' before repeating step 501.

If at step 501, the control system detects that the surgeon input device is in a gripping configuration, then it moves to step 502. At step 502, the control system commands maximum opposing forces to be applied to the driving elements of the end effector elements, so as to cause the end effectors to close with a maximum driving force. In the example of FIG. 2, this would be applying maximum driving forces to A2 and B1.

Following step 502, the control system moves to step 503 where it determines whether a yawing motion of the surgeon input device is detected. The yawing motion can be detected by sensors on the surgeon input device and/or sensors on the linkages connecting the surgeon input device to the console as described above with respect to FIG. 4. Whilst the control system carries out the determination of step 503, it continues to apply maximum opposing forces to the driving elements according to step 502.

If no yawing motion of the surgeon input device is detected, then the control system returns to step 503. The control system may wait for a time interval T" before repeating step 503.

If a yawing motion of the surgeon input device is detected at step 503, then the control loop moves to step 504. At step 504, the control system commands a reduced force to be applied to one of the driving elements which is causing the end effector elements to close, and commands the maximum force to continue to be applied to the other driving element which is causing the end effector elements to close. The reduced force applied to the one driving element is sufficient to enable the end effector to yaw as commanded by the surgeon input device. Taking the example of FIG. 2, if the surgeon input device was yawed in a clockwise direction, then the reduced force would be applied to B1 and the maximum force would be maintained on A2. This would enable the end effector 201 to rotate in a clockwise direction. If the surgeon input device was yawed in an anticlockwise direction, then the reduced force would be applied to A2 and the maximum force would be maintained on B1. This would enable the end effector 201 to rotate in an anticlockwise direction.

The factor by which the maximum force is reduced to the reduced force may be determined using a single-pole filter as described above with respect to FIG. 4. By reducing the force applied to one of the driving elements, the driving elements are able to yaw the end effector elements as described above with respect to FIG. 4.

Thus, the control loop of FIG. 5 does not prioritise maximising the gripping motion over a yawing motion. If a yawing motion is commanded by the surgeon input device whilst a gripping motion is occurring, the control system will reduce the force of the gripping motion enough to enable the yawing motion to be actioned. Thus, the control loop of FIG. 5 may be utilised to better mediate the interdependence of the gripping and yawing motion of an end effector. Gripping is prioritised, but yawing is enabled when commanded by reducing the gripping force.

Figure 6:
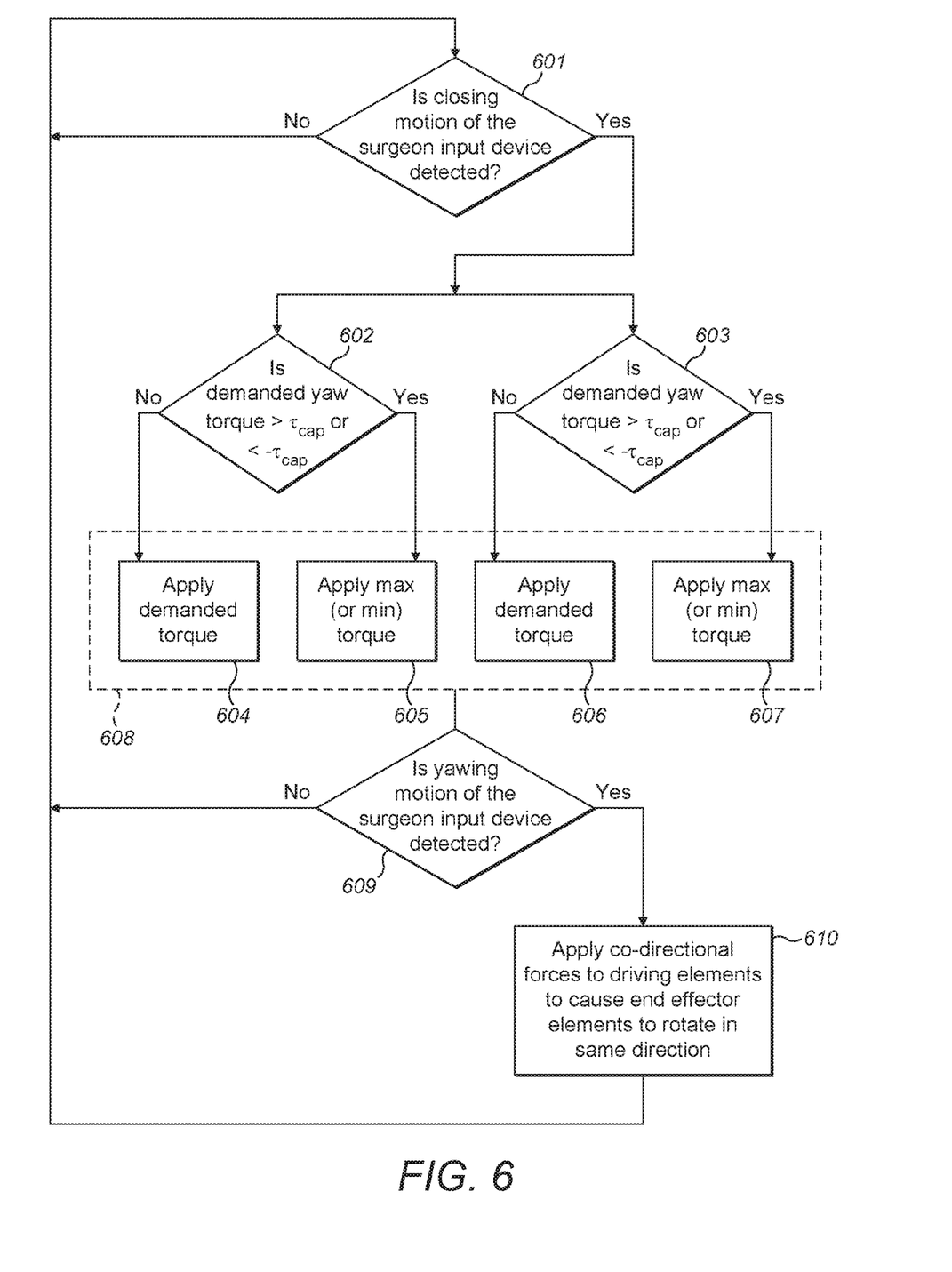
FIG. 6 is a flowchart of a method of controlling manipulation of another surgical instrument.

FIG. 6 illustrates a method implemented by the control system to mediate interdependence of the gripping and yawing motion of an end effector of either a gripping or cutting instrument.

At step 601, the control system detects whether there is a closing motion of the surgeon's input device. This is detected in the same manner as described with respect to FIG. 4. If at step 601, the control system does not detect a closing motion of the surgeon input device, then it returns to step 601. The control system may wait for a time interval T''' before repeating step 601.

If at step 601, the control system detects a closing motion of the surgeon input device, then it moves to steps 602 and 603. At steps 602 and 603, the control system determines if the end effector yaw torques demanded by the surgeon input device are greater than a threshold value, $\tau_{cap}$. Specifically, at step 602, the control system determines if the magnitude of the yaw torque demanded for the first end effector element is greater than $\tau_{cap}$. In other words, whether the absolute value of the yaw torque demanded for the first end effector is greater than $\tau_{cap}$ or less than $-\tau_{cap}$. And at step 603, the control system determines if the magnitude of the yaw torque demanded for the second end effector element is greater than $\tau_{cap}$. In other words, whether the absolute value of the yaw torque is greater than $\tau_{cap}$ or less than $-\tau_{cap}$.

The yaw driver torque $\tau_1$ for the first end effector element is the torque applied from the first drive assembly interface element to the first instrument interface element, which drives the first pair of driving elements A1, A2 to cause rotation of the first end effector element 209 about the first yaw axis 208.

The yaw driver torque 12 for the second end effector element is the torque applied from the second drive assembly interface element to the second instrument interface element, which drives the second pair of driving elements B1, B2 to cause rotation of the first end effector element 210 about the second yaw axis 212.

The control system may implement steps 602 and 603 as follows.

The demanded yaw torque at the end effector $\tau_{yd}$ may be defined as:

$$\tau_{yd} = \frac{(\tau_2 - \tau_1)}{2} \quad \text{(equation 4)}$$

The demanded spread torque at the end effector $\tau_{sd}$ may be defined as:

$$\tau_{sd} = \frac{(\tau_2 + \tau_1)}{2} \quad \text{(equation 5)}$$

A capped torque value is defined as:

$$\tau_{cap} = \max(\beta \tau_{max}, \tau_{max} - |\tau_{sd}|) \quad \text{(equation 6)}$$

The applied yaw torque $T_y$ and spread torque Ts values are defined as follows:

$$\tau_y = \text{CLAMP}(\tau_{yd}, -\tau_{cap}, \tau_{cap}) \quad \text{(equation 7)}$$

$$\tau_s = \text{CLAMP}(\tau_{sd}, -\tau_{max} + |\tau_y|, \tau_{max} - |\tau_y|) \quad \text{(equation 8)}$$

In other words, $\tau_y$ has the value of $\tau_{yd}$ unless $\tau_{yd} < -\tau_{cap}$ in which case it takes the value of $-\tau_{cap}$, or $\tau_{yd} > \tau_{cap}$ in which case it takes the value of $\tau_{cap}$. $\tau_s$ has the value of $\tau_{sd}$ unless $\tau_{sd} < -\tau_{max} + |\tau_y|$ in which case it takes the value of $-^{TM}_{ax} + |\tau_y|$, Or $\tau_{sd} > \tau_{max} \cdot |\tau_y|$, in which case it takes the value of $\tau_{max} \cdot |\tau_y|$.

Equations 7 and 8 are capped differently. The spread torque $\tau_s$ is prioritised. The spread torque's takes all of the available maximum torque $\tau_{max}$ minus the yaw torque $\tau_y$. The yaw torque is capped depending on a value β. β is a balance value which is set by the control system. 0<β<1. If β=0, then the opening and closing of the end effector elements is prioritised. All the available torque is used to provide the opening and closing motion of the end effector. If β=1, then the yaw motion of the end effector is prioritised. The available torque is used to provide the yawing motion of the end effector elements.

$\tau_{max}$ is a maximum torque value which is set by the control system. The maximum torque value may be dependent on the instrument type. The maximum torque value may be dependent on the capabilities of the motor providing the torque.

The applied yaw driver torque $\tau_{1a}$ for the first end effector element is given by:

$$\tau_{1a} = \tau_s - \tau_y \quad \text{(equation 9)}$$

The applied yaw driver torque $\tau_{2a}$ for the second end effector element is given by:

$$\tau_{2a} = \tau_s + \tau_y \quad \text{(equation 10)}$$

If the demanded spread torque and the demanded yaw torque of the end effector are between the threshold values shown in equations 7 and 8, then the answers to the questions of steps 602 and 603 are NO. In this case, the applied yaw driver torque $\tau_{1a}$ is the same as the demanded driver torque $\tau_1$, and the applied yaw driver torque $\tau_{2a}$ is the same as the demanded driver torque $\tau_2$. In this case, the control system moves to steps 604 and 606 where the demanded driver torques $\tau_1$ and $\tau_2$ are applied as the applied driver torques hi, and $\tau_{2a}$.

If the demanded spread torque and the demanded yaw torque of the end effector are greater than the maxima defined in equations 7 and 8 or less than the minima defined in equations 7 and 8, then the answers to the questions of steps 602 and 603 are YES. In this case, the applied yaw driver torque $\tau_{1a}$ is capped to a maximum (or minimum) yaw driver torque, and the applied driver torque $\tau_{2a}$ is capped to a maximum (or minimum) yaw driver torque as determined by the equations above. In this case, the control system moves to steps 605 and 607 where the maximum (or minimum) driver torques are applied as the applied driver torques $\tau_{1a}$ and $\tau_{2a}$.

On FIG. 6, steps 604, 605, 606 and 607 are all encased within a dashed step 608. This is to indicate that those ones of steps 604, 605, 606 and 607 which are implemented in a given iteration of the control method of FIG. 6 are done so in concert. For example, if the answer to both steps 602 and 603 is YES, then steps 605 and 607 are performed in concert. If the answer to both steps 602 and 603 is NO, then steps 604 and 606 are performed in concert. If the answer to step 602 is NO and the answer to step 603 is YES, then steps 604 and 607 are performed in concert. If the answer to step 602 is YES and the answer to step 603 is NO, then steps 605 and 606 are performed in concert.

Following step 608, the control system moves to step 609. At step 609, the control system determines if a yawing motion of the surgeon input device is detected. This may be done in the same manner as described with respect to FIG. 4.

If no yawing motion of the surgeon input device is detected, then the method returns to step 601, wherein the control system determines if a closing motion of the surgeon input device is detected. However, if a yawing motion of the surgeon input device is detected at step 609, then the control system moves to step 610, where it commands co-directional forces to be applied to the driving elements of the end effector elements so as to cause the end effector elements to rotate in the same direction in accordance with the yawing motion of the surgeon input device, as described with reference to FIG. 4.

The control system then returns to step 601 for a further iteration of the control loop.

Thus, the control loop of FIG. 6 may be utilised to better mediate the interdependence of the closing and yawing motions of an end effector. The torque applied to the driving elements during a closing motion is capped, so as to also enable the end effector elements to also be yawed.

In a further example, the method described with reference to steps 602 to 608 of FIG. 6 may be used in combination with the method of FIG. 4. For example, steps 602 and 608 of FIG. 6 may be used to determine the maximum forces in step 402 of FIG. 4. In this case, when determining the maximum forces to apply to the driving elements to cause the end effector elements to close, torque is reserved for yawing the end effector elements as described above with respect to FIG. 6. The force reduction value FRV described with reference to step 403 of FIG. 4 may, in this example, be the same as the balance value β of equation 6.

In a further example, the method described with reference to steps 602 to 608 of FIG. 6 may be used in combination with the method of FIG. 5. For example, steps 602 and 608 of FIG. 6 may be used to determine the maximum forces in step 502 of FIG. 5. In this case, when determining the maximum forces to apply to the driving elements to cause the end effector elements to close, torque is reserved for yawing the end effector elements as described above with respect to FIG. 6. Only if that reserved torque is insufficient for the subsequently demanded yawing motion of step 503, does the control system reduce the forces applied to the driving elements as described with reference to step 504. The force reduction value FRV described with reference to step 504 of FIG. 5 may, in this example, be the same as the balance value β of equation 6.

The end effector may take any suitable form. For example, the end effector could be a pair of curved scissors, an electrosurgical instrument such as a pair of monopolar scissors, a needle holder, a pair of jaws, or a fenestrated grasper.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system configured to control manipulation of a surgical instrument in response to manipulation signals of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system comprising a processor configured to:

respond to a closing motion of the surgeon input device by commanding signals of maximum forces to be applied to the first and second pairs of driving elements, so as to cause the first and second end effector elements to rotate in opposing rotational directions towards each other with a maximum closing force; and on detecting that the closing motion of the surgeon input device has ceased, commanding signals of a reduction in the force applied to the first and second pairs of driving elements, thereby enabling both the first and second end effector elements to be rotated in the same rotational direction in response to a yawing motion of the surgeon input device.

2. A control system as claimed in claim 1, wherein the surgeon input device comprises a body and a trigger, and the closing motion of the surgeon input device comprises a movement of the trigger relative to the body.

3. A control system as claimed in claim 2, wherein the closing motion of the surgeon input device comprises a rotation of the trigger towards the body or a linear translation of the trigger relative to the body.

4. A control system as claimed in claim 2, wherein the yawing motion comprises a rotation of the body of the surgeon input device.

5. A control system as claimed in claim 2, wherein the surgeon input device comprises a sensor configured to detect the position of the trigger relative to the body, wherein the control system is configured to detect that the closing motion of the surgeon input device has ceased if the sensed position of the trigger relative to the body is constant.

6. A control system as claimed in claim 5, further comprising a single-pole filter which is configured to receive a signal of a velocity of the trigger derived from the sensed positions of the trigger relative to the body, and output a force reduction factor.

7. A control system as claimed in claim 1, wherein the processor is further configured to command signals of maximum forces to be applied to the first and second pairs of driving elements by:

applying a first maximum force to a first driving element of the first pair of driving elements, and applying a second maximum force to a second driving element of the second pair of driving elements, wherein the magnitudes of the first and second maximum forces are the same.

8. A control system as claimed in claim 1, wherein the processor is further configured to command signals of maximum forces to be applied to the first and second pairs of driving elements by:

applying a first maximum force to a first driving element of the first pair of driving elements, and applying a second maximum force to a second driving element of the second pair of driving elements, wherein the magnitudes of the first and second maximum forces are different.

9. A control system as claimed in claim 8, wherein the processor is further configured to respond to a yawing motion of the surgeon input device by commanding signals of:
- a first force to be applied to the first driving element of the first pair of driving elements, and
- a second force to be applied to the first driving element of the second pair of driving elements,
- wherein the magnitudes of the first and second forces are the same.

10. A control system as claimed in claim 1, wherein the processor is further configured to command signals of a reduction in the force applied to the first and second pairs of driving elements by a function dependent on instrument type and/or trigger motion.

11. A control system as claimed in claim 1, wherein the maximum closing force enables cutting of an object between the first and second end effector elements.

12. A control system as claimed in claim 1, wherein upon the control system detecting that the closing motion of the surgeon input device has ceased, the first and second end effector elements abut each other in a closed configuration.

13. A control system configured to control manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system comprising a processor configured to:
- respond to a signal of a gripping configuration of the surgeon input device by commanding signals of maximum forces to be applied to the first and second pairs of driving elements, so as to cause the first and second end effector elements to rotate in opposing rotational directions towards each other with a maximum closing force; and
- on detecting a yawing motion of the surgeon input device, commanding signals of a reduction in the force applied to a first driving element of the first pair of driving elements, thereby enabling both the first and second end effector elements to be rotated in the same rotational direction.

14. A control system as claimed in claim 13, wherein on detecting the yawing motion of the surgeon input device, the control system is configured to continue commanding signals of the maximum force to be applied to a second driving element of the second pair of driving elements.

15. A control system as claimed in claim 13, wherein the surgeon input device comprises a body and a trigger, and the surgeon input device is in a gripping configuration when the trigger has a position relative to the body that is within a specified range.

16. A control system as claimed in claim 15, wherein the gripping configuration of the surgeon input device comprises: a rotational position of the trigger relative to the body that is within a specified range of rotational positions or a linear position of the trigger relative to the body that is within a specified range of linear positions.

17. A control system as claimed in claim 15, wherein the yawing motion comprises a rotation of the body of the surgeon input device.

18. A control system as claimed in claim 17, further comprising a single-pole filter configured to receive a velocity of the trigger derived from the sensed positions of the trigger relative to the body, and output a force reduction factor.

19. A control system as claimed in claim 15, wherein the surgeon input device comprises a sensor configured to detect the position of the trigger relative to the body.

20. A control system as claimed in claim 13, wherein the processor is further configured to command signals of maximum forces to be applied to the first and second pairs of driving elements by:
- applying a first maximum force to a first driving element of the first pair of driving elements, and
- applying a second maximum force to a second driving element of the second pair of driving elements,
- wherein the magnitudes of the first and second maximum forces are the same.

21. A control system as claimed in claim 13, configured to command signals of maximum forces to be applied to the first and second pairs of driving elements by:
- applying a first maximum force to a first driving element of the first pair of driving elements, and
- applying a second maximum force to a second driving element of the second pair of driving elements,
- wherein the magnitudes of the first and second maximum forces are different.

22. A control system as claimed in claim 13, wherein the processor is further configured to command signals of a reduction in the force applied to the first and second pairs of driving elements by a function dependent on instrument type and/or trigger motion.

23. A control system as claimed in claim 13, wherein the maximum closing force enables gripping of an object between the first and second end effector elements.

24. A control system configured to control manipulation of a surgical instrument in response to manipulation signals of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system comprising a processor configured to:
- respond to a closing motion signal of the surgeon input device by:
- comparing a demanded first yaw torque for the first end effector element to a first maximum yaw torque, and comparing a demanded second yaw torque for the second end effector element to a second maximum yaw torque, and
- only if the demanded first yaw torque is less than the first maximum yaw torque, and the demanded second yaw torque is less than the second maximum yaw torque, commanding signals of the demanded first yaw torque to be applied to the first end effector element and signals of the demanded second yaw torque to be applied to the second end effector element, so as to cause the first and second end effector elements to rotate in opposing rotational directions towards each other with a closing force; and
- on detecting a yawing motion of the surgeon input device, command signals of co-directional forces to be applied to the first and second pairs of driving elements, thereby causing both the first and second end effector elements to be rotated in the same rotational direction.

25. A control system as claimed in claim 24, wherein the processor is further configured to, if the demanded first yaw torque is greater than the first maximum yaw torque, and the demanded second yaw torque is greater than the second maximum yaw torque, command signals of the first maximum yaw torque to be applied to the first end effector element and signals of the second maximum yaw torque to be applied to the second end effector element, so as to cause the first and second end effector elements to rotate in opposing rotational directions towards each other with a closing force.

26. A control system as claimed in claim 24, wherein the processor is further configured to further respond to a closing motion signal of the surgeon input device by:
comparing the demanded first yaw torque for the first end effector element to a first minimum yaw torque, and comparing a demanded second yaw torque for the second end effector element to a second minimum yaw torque, and
only if the demanded first yaw torque is greater than the first minimum yaw torque, and the demanded second yaw torque is greater than the second minimum yaw torque, commanding signals of the demanded first yaw torque to be applied to the first end effector element and signals of the demanded second yaw torque to be applied to the second end effector element, so as to cause the first and second end effector elements to rotate in opposing rotational directions towards each other with a closing force.

27. A control system as claimed in claim 26, wherein the processor is further configured to, if the demanded first yaw torque is less than the first minimum yaw torque, and the demanded second yaw torque is less than the second minimum yaw torque, command signals of the first minimum yaw torque to be applied to the first end effector element and signals of the second minimum yaw torque to be applied to the second end effector element, so as to cause the first and second end effector elements to rotate in opposing rotational directions towards each other with a closing force.

\* \* \* \* \*